United States Patent [19]

Amplatz

[11] 4,355,409

[45] Oct. 19, 1982

[54] SCANNING X-RAY SYSTEM

[76] Inventor: Kurt Amplatz, 10 Evergreen Rd., St. Paul, Minn. 55110

[21] Appl. No.: 253,181

[22] Filed: Apr. 13, 1981

Related U.S. Application Data

[63] Continuation of Ser. No. 71,184, Aug. 31, 1979, abandoned.

[51] Int. Cl.³ .............................................. G03B 41/16
[52] U.S. Cl. .................................... 378/146; 378/197
[58] Field of Search ............... 250/523, 505, 320, 321, 250/322, 323, 445 R, 446, 447, 448, 449

[56] References Cited

U.S. PATENT DOCUMENTS

| | | | |
|---|---|---|---|
| 2,511,853 | 6/1950 | Kaiser | 250/323 |
| 3,984,684 | 10/1976 | Winnek | 250/313 |
| 4,096,391 | 6/1978 | Barnes | 250/505 |
| 4,097,748 | 6/1978 | Monovoisin | 250/505 |

OTHER PUBLICATIONS

Vallebona, "Una modalita di tecnica per la dissociazione radiografica delle ombre applicate allo studio del cranio", *Radiol Med* 27: 1090–2097, Sep. 1930.
Bozetti, "La realizzazione practica della stratigrafia", *Radiol Med* 22: 257–267, 1935.
Heckmann, "Die Roentgenperspektive und ihre umwandlung durch eine neue Aufnahmenik", *Fortschr Roentgenstr* 60: 140,139.
Paatero "A New Tomographic Method For Radiographing Curved Outer Surfaces", *Acta Radiol* 32: 177, 1949.
Spiegler, Breckenridge, "Imaging of Focal Spots by Means of the Star Test Pattern", *Radiology* 102: 679–684 Mar. 1972.
"Investigations of Moving Slit Radiography", Sorenson et al. Radiology, Sep. 1976, pp. 705–711.

*Primary Examiner*—Craig E. Church
*Attorney, Agent, or Firm*—Kinney, Lange, Braddock, Westman and Fairbairn

[57] ABSTRACT

An x-ray apparatus uses an x-ray tube which is pivoted about a pivot axis to provide scanning of an x-ray beam. The pivot axis passes essentially through the center of the focal spot on the target surface of the anode of the tube, is essentially perpendicular to the anode-cathode axis, and is essentially parallel to a film plane defined by the x-ray film. The scanning of the x-ray beam by pivoting the x-ray tube results in improved systems for standard radiography, linear tomography, and large-scale angiography. In standard radiography and large scale angiography systems, moving primary and secondary slots synchronized with the pivoting of the x-ray tube provide efficient removal of secondary radiation. In linear tomography systems, the object and film are moved synchronously with the pivoting of the x-ray tube, and primary and secondary slots which are stationary remove secondary radiation.

18 Claims, 19 Drawing Figures

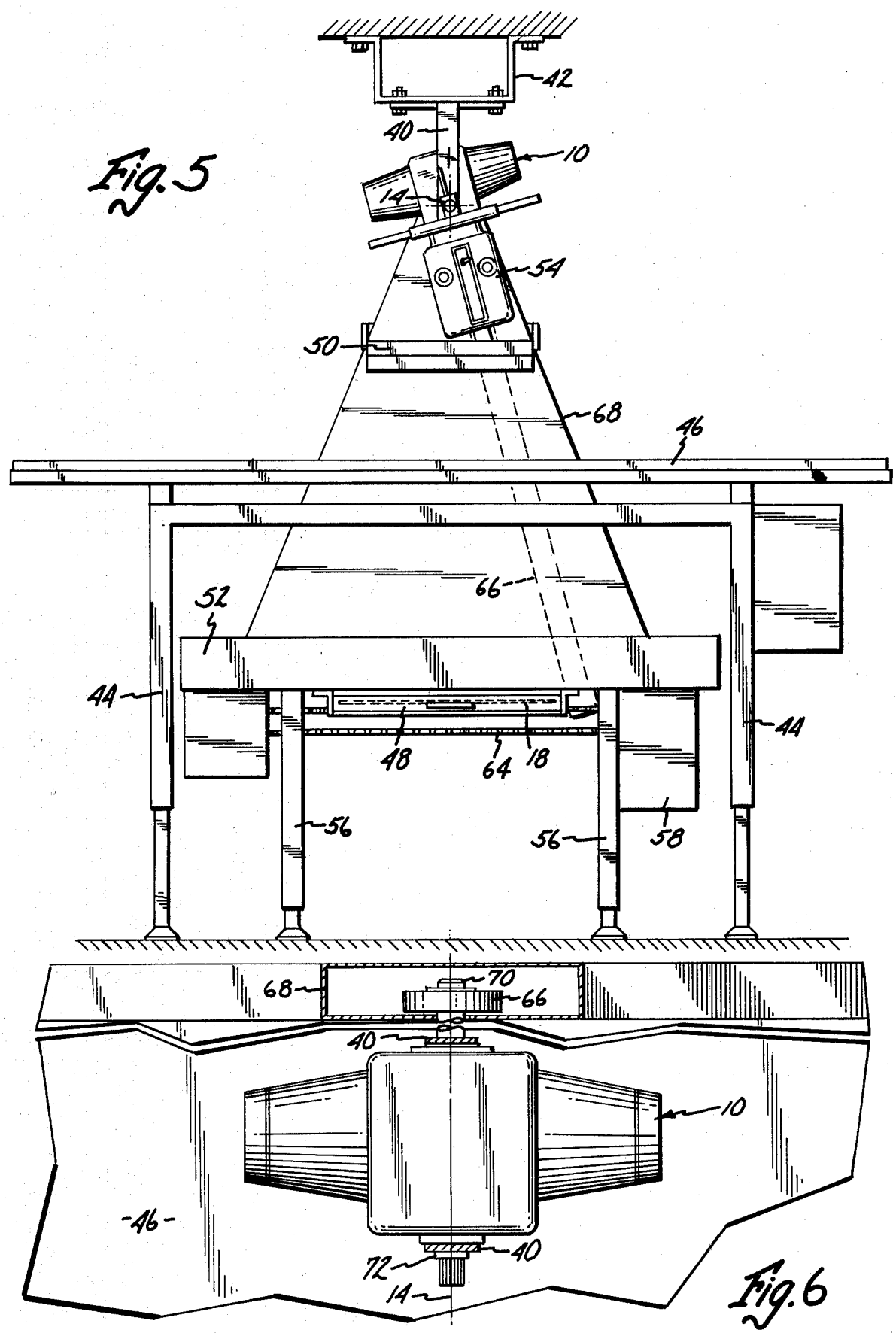

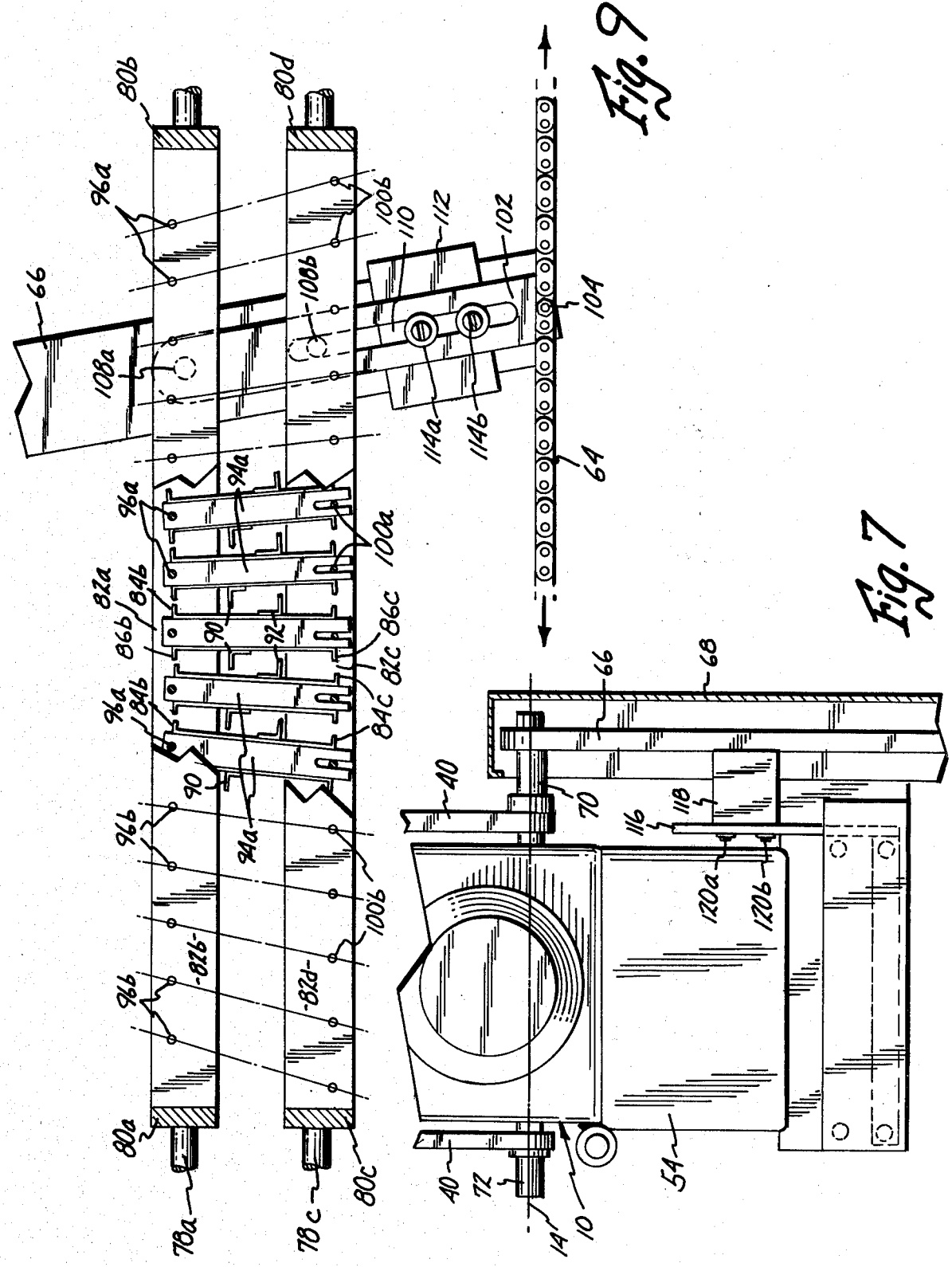

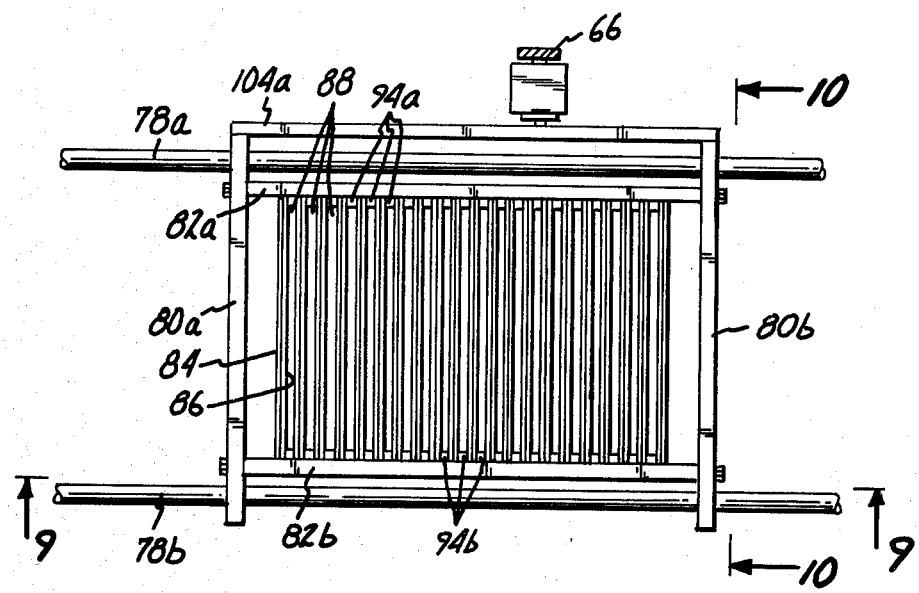
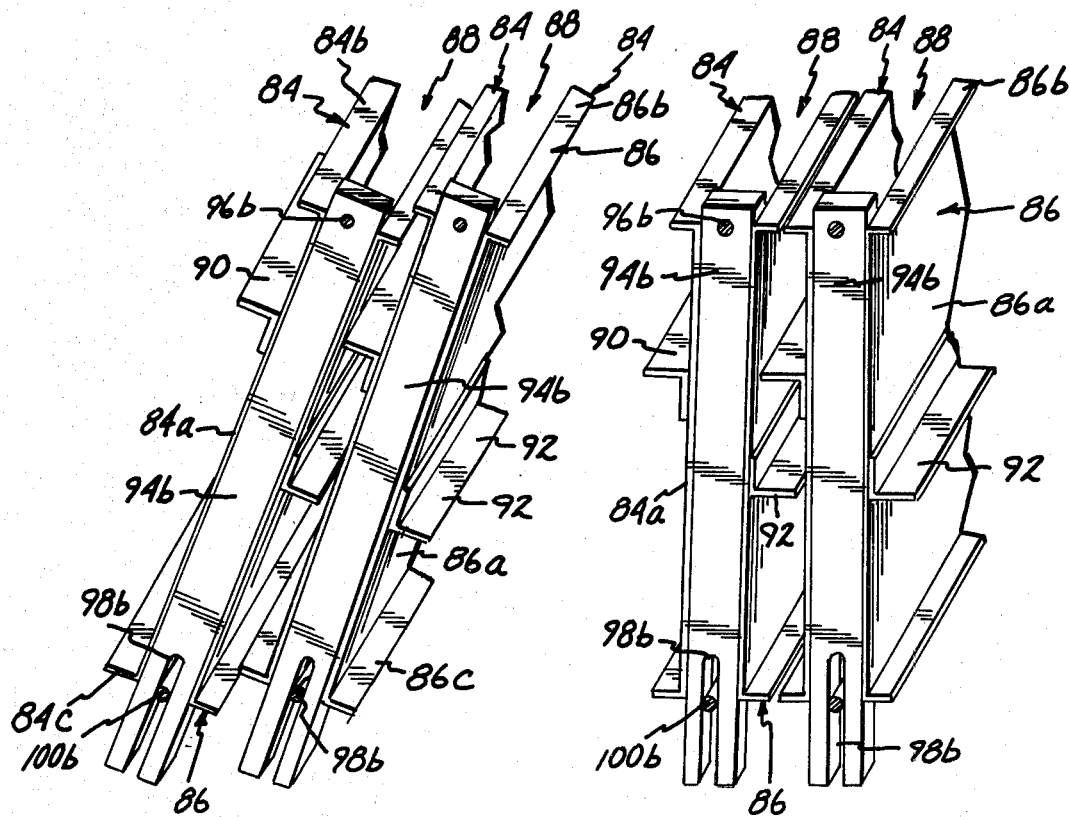

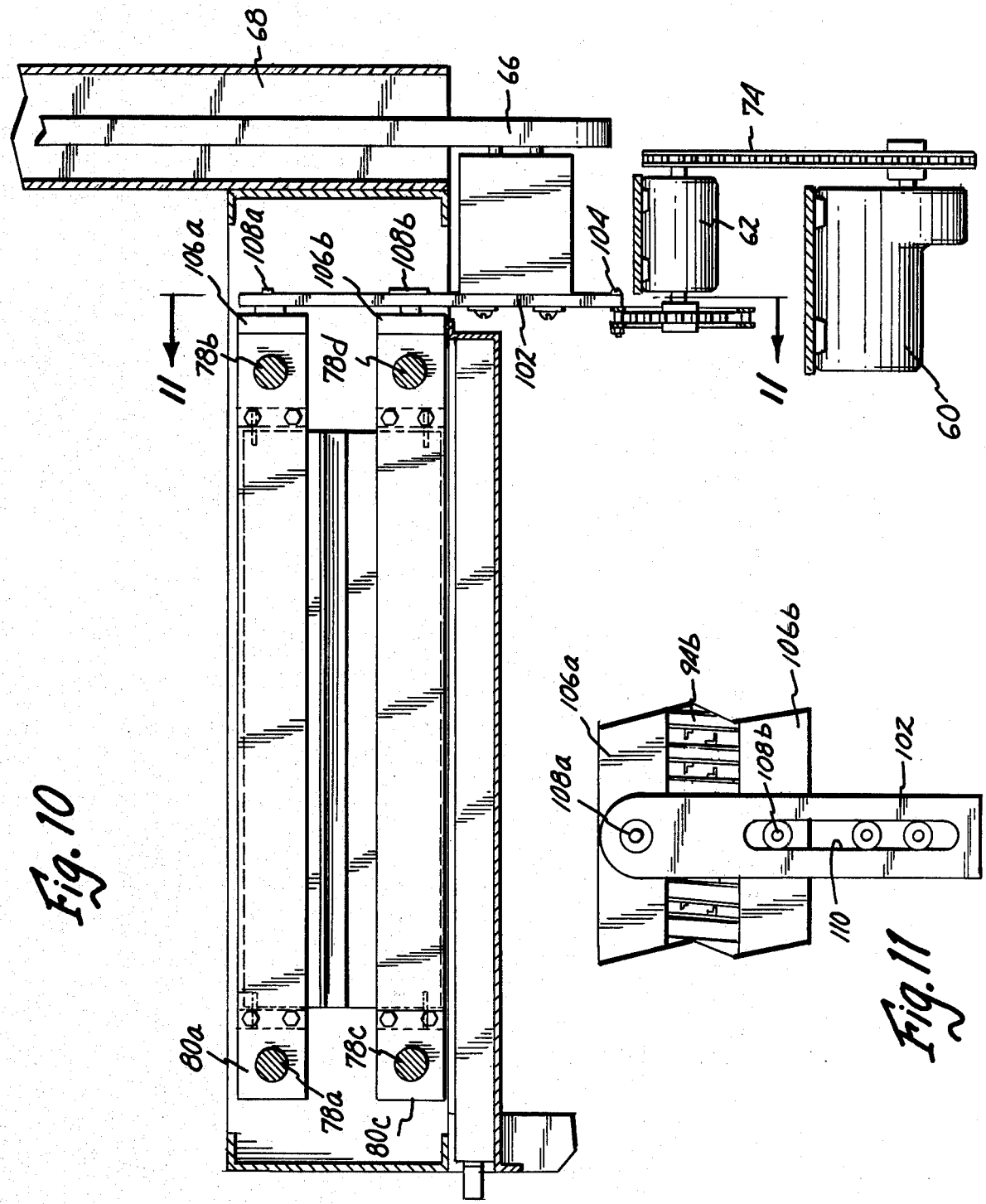

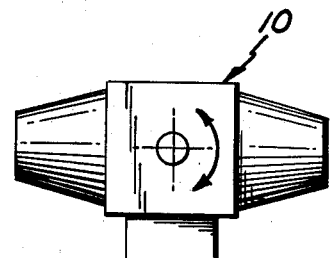
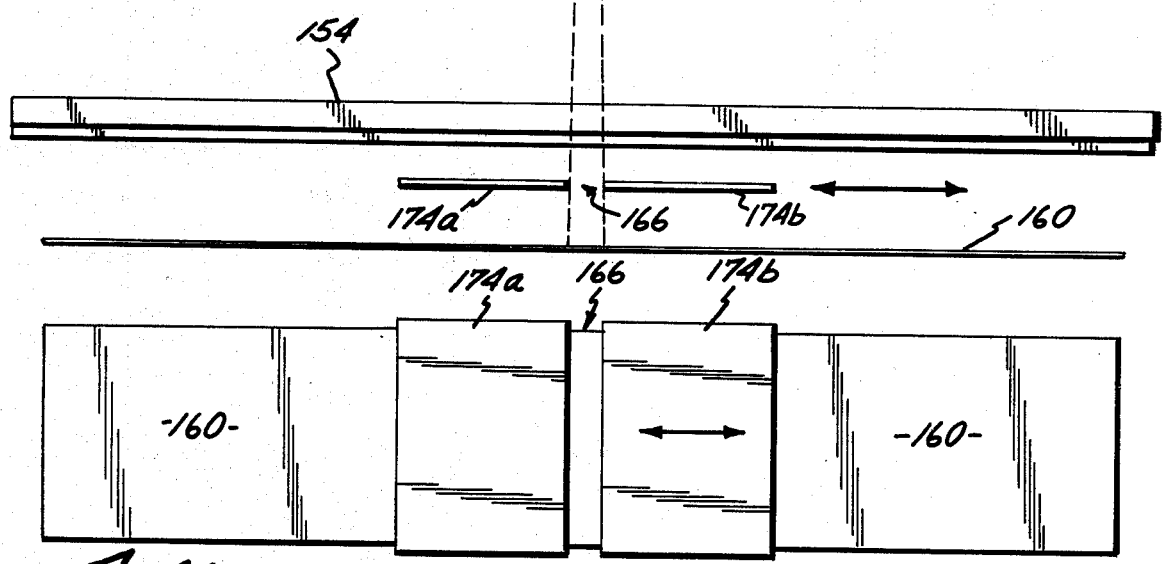

SCANNING X-RAY SYSTEM

This is a continuation of application Ser. No. 071,184, filed Aug. 31, 1979 now abandoned.

BACKGROUND OF THE INVENTION

1. Field of the Invention

The present invention relates to radiography. In particular, the present invention is an improved scanning x-ray system useful in a wide range of radiographic systems.

2. Description of the Prior Art

Radiographic systems typically include an x-ray tube which emits x-rays. These x-rays are directed through an object to be studied (such as a portion of the human body) and onto an x-ray film. The x-ray tube typically includes an anode and a cathode.

When a very high voltage is applied between the anode and cathode, an electron stream is directed from the cathode along an anode-cathode axis and onto a target portion of the anode. The small area of the target which the electrons strike is called the focal spot, and is the source of the x-rays emitted by the tube.

The impact of the electrons at the focal spot generates both x-rays and a significant amount of heat. This heat must be dissipated so that the target, and therefore the tube, is not destroyed.

The quality of a radiographic image depends on the size and configuration of the focal spot. The smaller the focal spot, the better the detail of the image. Ideally the focal spot should be a point source. However, since a large spot can tolerate more heat than a small one, reducing the focal spot to a point source is not feasible without reducing the instantaneous heat loading capacity to levels which would preclude use in a clinical radiographic system.

One common technique for reducing the effective size of the focal spot is by using the line focus principle and rotating the anode. The line focus principle uses a target which is at an angle with respect to a plane perpendicular to the anode-cathode axis. The electron stream is focused on a narrow rectangle on the target. When the rectangular focal spot is viewed from below the anode, the focal spot is essentially square, and the effective area of the focal spot is only a fraction of its actual area. The length of the projected focal spot can be decreased by making the target angle smaller. However, a small target angle compromises field coverage. For adequate coverage in angiography, x-ray tubes having an 11° or 12° target are presently being used. For standard radiography, the target angle has to be larger to allow the coverage of a 35.9×43.6 centimeter (14×17 inch) radiograph at 1.02 meters (40 inches).

Further increases in the capacity of the anode to withstand heat have been achieved with rotating anode tubes. In these tubes, the anode is disk shaped, and has a beveled target area near its end. The cathode is arranged to direct the electron stream against the beveled target area of the disk, while the disk rotates. The position of the focal spot remains fixed in space while the anode rotates, thereby increasing the effective area being exposed to the electron beam, while maintaining the focal spot at a much smaller area than is possible with a stationary anode.

Since the introduction of the high speed rotating anode x-ray tubes, little progress has been made in significantly increasing instantaneous heat tube loading. As a result, the effective focal spot size for standard radiographic systems has not been significantly decreased. There is a continuing need for radiographic systems which produce superior radiographs with high resolution, increased contrast, and less patient exposure than in the prior art standard radiographic systems.

Tomography is a special radiographic technique in which a distinct image of a selected plane through the object is produced, while images of structures that lie on opposite sides of the plane are blurred. The value of tomography in clinical practice is well established.

In most presently used tomographic systems the patient remains stationary, and the x-ray tube and film cassette are moved. In these types of systems, the tube is typically mounted on a long arm, and as it is moved there is unavoidable vibration. As a result, the apparent focal spot size increases due to the vibration, thereby producing geometric unsharpness.

It has been known for many years that tomographs (and in particular laminographs) can be obtained by moving the object and film cassette and keeping the radiographic tube stationary. This principle was introduced by Vallebona in "Una modalita di tecnica per la dissociazione radiografica delle ombre applicate allo studio del cranio", *Radiol Med* 17: 1090–1097, September 1930, and was perfected by Bozetti, who actually built such an apparatus. See "La realizzazione practica della stratigrafia", *Radiol Med* 22: 257–267, 1935. With Bozetti's laminogram, the patient rotated about a craniocaudal axis; and the radiographic plate moved synchronously. This apparatus, however, never became popular because structures lying transversely (such as the ribs) could not be sufficiently blurred.

Previously, tomography with a linear patient motion was not possible because of the limited field coverage of standard radiographic tubes. If the object and film are moved synchronously, the object would move out of the x-ray beam. This method was suggested by Heckmann in "Die Roentgenperspektive und ihre umwandlung durch eine neue Aufnahmetechnik", *Fortschr Roentgenstr* 60: 140, 139. Heckmann used a stationary x-ray tube with the patient and cassette moving in opposite directions. With this technique, only a very small area of the body could be examined, and therefore the method was impractical.

Another form of tomography which has presently found use is pantomography, which is described by Pantero in "A new tomographic method for radiographing curved outer surfaces", *Acta Radiol* 32: 177, 1949. In this system, the patient and a curved x-ray film rotate in opposite directions to yield a true laminogram. This type of laminography is useful only for the examination of the jaw.

Conventional tomography, therefore, has the shortcoming of poor resolution due to vibration of the x-ray tube, poor contrast due to a high fog level, and restriction to cuts parallel to the patient table. It is desirable to improve further the quality and diagnostic yield of tomography, and to provide means by which tomograms can be made of organs difficult to image because they do not lie in a plane parallel to the patient table.

Still another radiographic technique is angiography—the study of blood vessels. In some cases it is necessary to study the arteries from the abdomen of a patient all the way down to his toes. This large field coverage has necessitated special angiographic systems. In many cases the x-ray tube in an angiographic system must be mounted a large distance from the patient table in order to achieve the desired field coverage. This has required an extremely high ceiling of the room within which the angiographic system is located. In some cases, an entire radiology department must be specially designed to accommodate a room with an extremely high ceiling in order to house the angiographic system.

There is a continuing need for an angiographic system which provides the necessary wide field coverage and yet can be housed in a conventional room, rather than requiring a room with an extremely high ceiling.

SUMMARY OF THE INVENTION

The present invention is an improved x-ray apparatus. In the present invention pivoting means pivot an x-ray tube about a pivot axis to provide scanning of the x-ray beam produced by the x-ray tube. The pivot axis passes essentially through the center of the focal spot in the x-ray tube, is essentially perpendicular to the anode-cathode axis, and is essentially parallel to the film plane defined by the x-ray film. The x-ray apparatus of the present invention yields significantly improved results in a wide range of radiographic applications, including standard radiology, linear tomography, and large field angiography.

The present invention preferably also includes primary slot means positioned between the x-ray tube and the object, and secondary slot means positioned between the object and the x-ray film plane. Means are provided for causing relative motion of the primary and secondary slot means with respect to the object and the x-ray film. This relative motion is synchronized with the pivoting of the x-ray tube.

In standard radiographic systems and angiographic systems utilizing the present invention, the primary and secondary slot means are preferably driven in synchronism with the pivoting of the x-ray tube. In linear tomographic systems utilizing the present invention, the object and the film are driven in synchronism with the pivoting of the x-ray tube, while the primary and secondary slot means remain stationary.

BRIEF DESCRIPTION OF THE DRAWINGS

FIG. 5 is a front elevational view of a preferred embodiment of a standard radiography system utilized in the present invention.

FIG. 6 is a top view showing the x-ray tube of the apparatus of FIG. 5.

FIG. 7 is a view along line 7—7 of FIG. 5 showing the x-ray tube, the primary slot device, and the pivot arm which drives the tube and the primary slot device.

FIG. 8 is a top view of the secondary slot device.

FIG. 9 is a section along line 9—9 of FIG. 8 showing the secondary slots and drive mechanism.

FIG. 10 is a section along line 10—10 of FIG. 8.

FIG. 11 is a section along line 11—11 of FIG. 10.

FIGS. 12A and 12B illustrate operation of the secondary slot device.

FIG. 15 is a diagrammatic front elevation illustrating the operation of the apparatus of FIG. 13.

FIG. 16 is a top view illustrating the operation of the secondary slot and its relation to the film in the system of FIGS. 13 and 15.

DETAILED DESCRIPTION OF THE PREFERRED EMBODIMENTS

Figure 1:
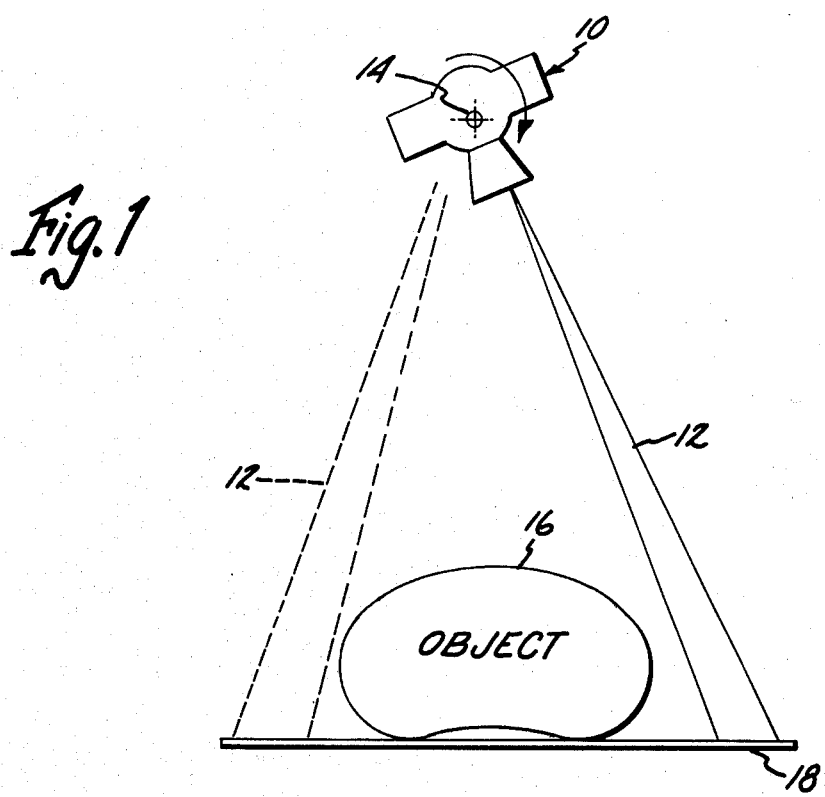
FIG. 1 is a diagrammatic view illustrating the pivoting tube scanning x-ray apparatus of the present invention.
Figure 2:
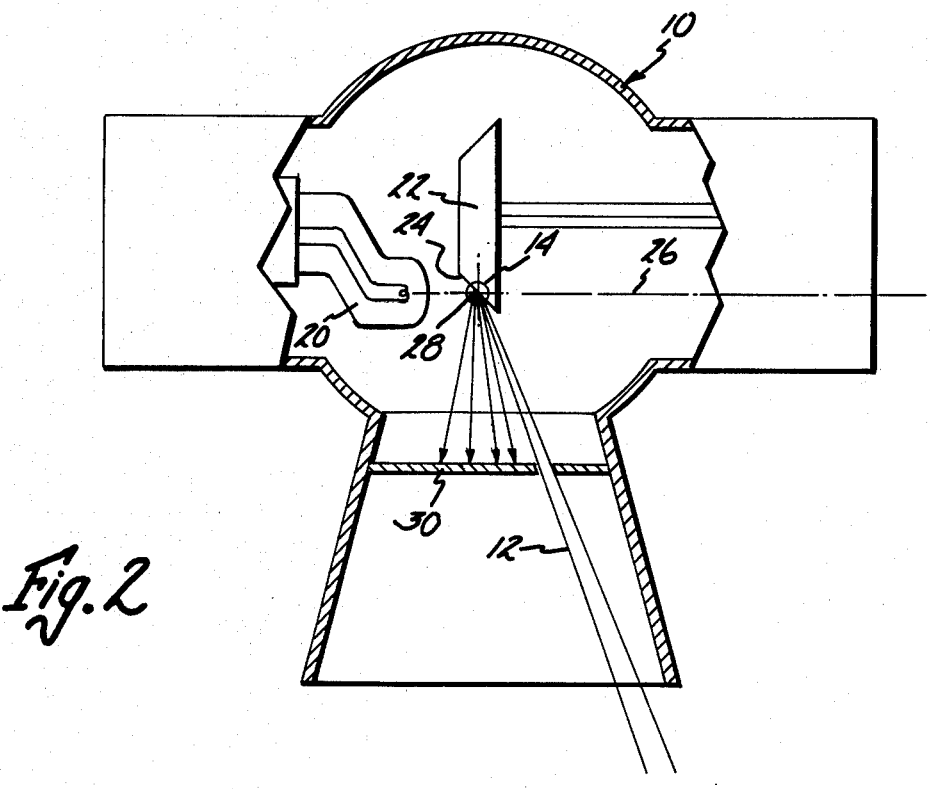
FIG. 2 is a partial sectional view of an x-ray tube illustrating the pivot point utilized in the present invention.

FIGS. 1 and 2 show the basic concept of the scanning x-ray system of the present invention. As shown in FIG. 1, x-ray tube 10 provides a narrow beam of x-rays 12. Tube 10 is pivoted about pivot axis 14, so that beam 12 is scanned across object 16 and x-ray sensitive film 18 to produce an x-ray exposure of x-ray film 18.

FIG. 2 shows a preferred embodiment of tube 10. As shown in FIG. 2, tube 10 is a rotating anode type x-ray tube having a cathode 20 and a rotating anode 22. Anode 22 is a beveled tungsten disk having a target surface 24 oriented at an angle with respect to anode-cathode axis 26. Electrons from cathode 20 are directed onto target surface 24 at a focal spot 28, and x-rays 12 are emitted from focal spot 28. As shown in FIG. 2, aperture stop 30 selects only those rays emanating from the most shallow portion of target 24 (i.e. furthest from cathode 20).

In the present invention, tube 10 is pivoted about pivot axis 14 and provides scanning of x-ray beam 12. Pivot axis 14 is perpendicular to anode-cathode axis 26, is parallel to the plane of film 18, and passes exactly through the center of focal spot 28. As a result, focal spot 28 remains effectively stationary and no loss of sharpness occurs from the pivotal movement of the tube.

One important advantage of the present invention is that it permits the focal spot size to be reduced without significantly compromising the tube heat loading. First, because the beam 12 is scanned, the field coverage of beam 12 need not be the entire field required to be covered. As a result, the effective size of the focal spot can be reduced by biasing the grid electrode (not shown in FIG. 2) of the x-ray tube 10.

Second, because the required field coverage of beam 12 is smaller due to scanning, the target angle of target 24 with respect to anode-cathode axis 26 can be reduced significantly in comparison to the normal target angle required. This also reduces the effective size of focal spot 28, thereby increasing resolution.

Third, aperture stop 30 may be used to select only a narrow portion of the x-ray beam 12 emanating from the most shallow portion of the target (i.e. the portion furthest from cathode 20). This eliminates the optical density gradient (heel effect) which is normally present in standard radiography.

Fourth, due to scanning of the beam 12 by pivoting tube 10, the resolution gradient normally present along the anode-cathode axis in prior art systems is eliminated.

In one successful embodiment of the present invention a standard, grid controlled General Electric Maxi-ray 100 tube with a 6.5° target and 0.3 and 0.6 mm nominal focal spot sizes was used. The target heat loading capacity was rated as 20 kW and 60 kW for the 0.3 and 0.6 mm nominal focal spot sizes, respectively. This type of x-ray tube permitted a negative bias voltage varying from 0 to 400 volts to be applied to the grid. The generator for driving the x-ray tube was a three-phase, twelve pulse unit.

The x-ray tube 10 was mounted on a stand which permitted rotation of tube 10 about pivot axis 14 passing exactly through the center of the focal spot 28. Pivot axis 14 was perpendicular to the anode-cathode axis 26 and parallel to the film plane (as is illustrated schematically in FIGS. 1 and 2). The manufacturer of the x-ray tube indicated the approximate location of focal spot 28 on the outside of the tube housing. Finer adjustments were accomplished by using magnified radiographs of fine wires and a paralactic correction technique. By this method, tube 10 was mounted so that pivot axis 14 passed exactly through the center of the focal spot 28.

Figure 3:
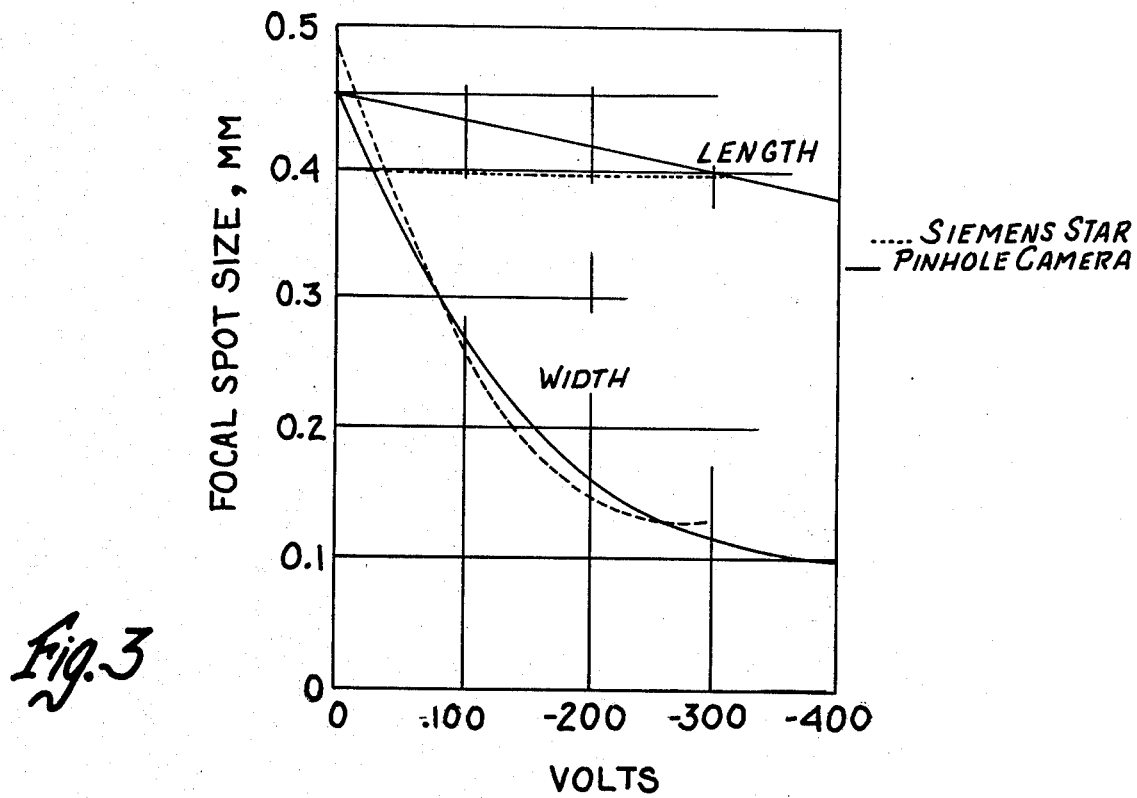
FIG. 3 is a graph showing focal spot size as a function of applied grid voltage.

The dimensions of the smaller (0.3 mm nominal) focal spot in the unbiased mode were measured with a star resolution pattern using the Spiegler and Breckenridge method and were found to be 0.5×0.5 mm. See, Spiegler P., Breckenridge W.C.: "Imaging of Focal Spots by Means of the Star Test Pattern", *Radiology* 102: 679–684, March 1972. When the grid was biased, the pin hole images obtained showed dramatic reduction in the width of the focal spot. No significant further shrinkage of the focal spot was obtained with negative grid biases of more than 200 volts. The measurement of the focal spot with 200 volts negative grid bias showed a 0.15 mm width and only a slight change in its length, from 0.40 to 0.36 mm. The change in dimensions of the focal spot with varying tube bias is shown in FIG. 3. Both pin hole camera measurements and Siemens star measurements are shown.

The striking reduction of the width of the focal spot was also demonstrated by taking a magnification view of the star pattern. Resolution increased dramatically, but in only one dimension. However, if the star pattern was radiographed toward the anode side of the x-ray tube, both dimensions of the calculated focal spot size were reduced to 0.2 mm. By using aperture stop 30 (as shown in FIG. 2) and thereby using only the portion of the x-ray beam toward the anode side while masking out the remainder of the beam, a field of only 5 cm (2 inches) long is covered, but the width of the beam was not altered. A field coverage of 43.6×5 cm (17×2 inches), of course, is not useful in the prior art standard radiographic systems. In the present invention, however, an area of 35.9×43.6 centimeter (14×17 inches) or larger can easily be covered by this narrow beam (i.e. 17×2 inches) by pivoting tube 10 about pivot axis 14 to scan beam 12 across the area.

As discussed previously, the quality of a radiographic image depends largely on the size and configuration of the focal spot. This is particularly true for a magnified image. Although ideally the focal spot should be a point source, this is not feasible without reducing the instantaneous heat load capacity to levels precluding clinical use. This approach was recently chosen by one of the microfocus tube manufacturers; but it allows a tube rating of only 2 mA at 100 kV, seriously limiting its clinical application. The length of the projected focal spot can be decreased by making the target angle small because of the line focus principle, but a small target angle compromises field coverage. In the prior art radiographic systems, x-ray tubes of 11° or 12° target angle are used to provide adequate field coverage. For standard radiography, the target angle required has been even larger to allow for coverage of a 35.9×43.6 centimeter (14×17 inch) radiograph at 1.02 meter (40 inch).

Figure 4:
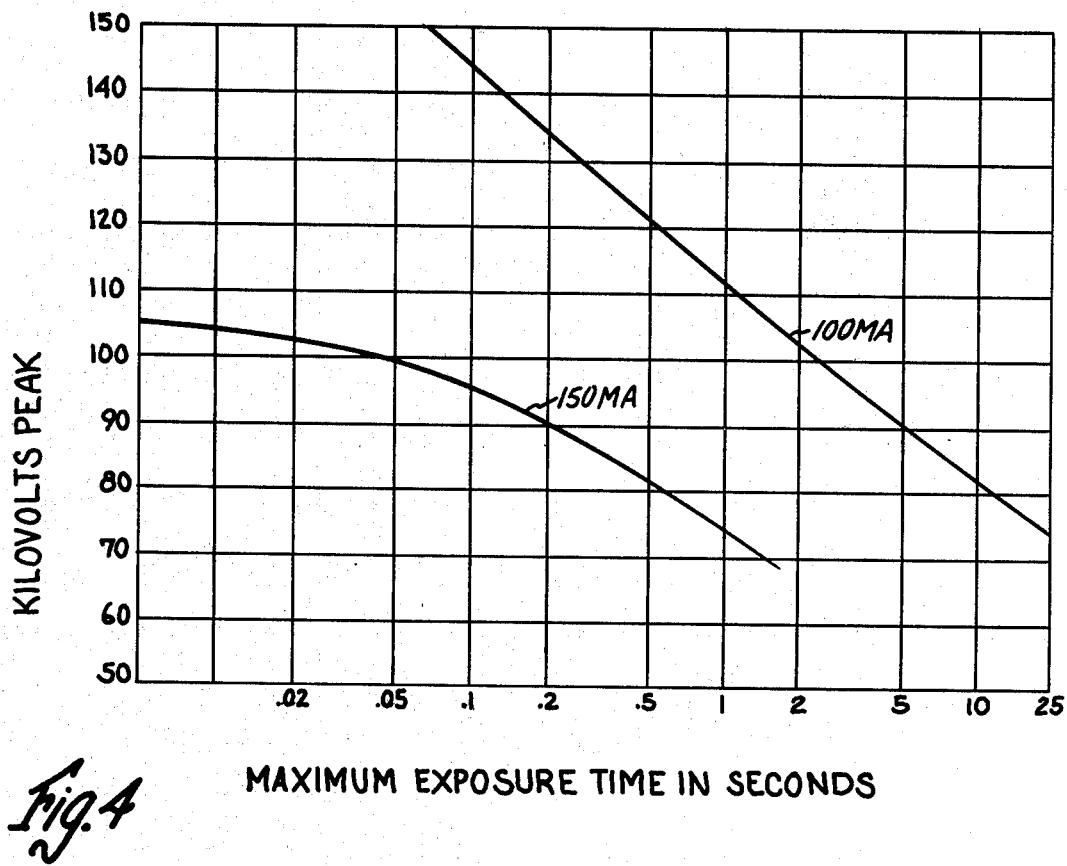
FIG. 4 is a graph showing maximum exposure times in seconds for various peak voltages for a x-ray tube biased at −200 volts grid bias.

The undesirable configuration of the 0.3 millimeter focal spot of the unbiased General Electric Maxi-ray 100 tube was reduced to a uniform 0.1 millimeter focal spot by a negative grid voltage. Although the application of the negative grid bias voltage decreased the tube output somewhat, a clinically acceptable tube rating was still maintained, as shown in FIG. 4, which is a tube rating chart of the effective 100 micron focal spot using a −200 volt grid bias. It is apparent from FIG. 4 that with a negative bias of −200 volts, an x-ray exposure of 2 seconds at 100 kV and 100 mA is feasible.

In the prior art, standard radiographs have not only a considerable gradient of resolution along the anode-cathode axis, but there is also an optical density gradient (heel effect). By pivoting x-ray tube 10 about pivot axis 14, (as illustrated in FIG. 1 and 2) the resolution and density gradients disappear. By biasing the 0.6 mm focal spot and pivoting the x-ray tube, a 0.3×0.3 mm effective focal spot was obtained, thus allowing high quality standard magnification radiography with a magnification factor up to 1.8 to 2. By applying the bias to the 0.3 mm nominal focal spot, it was possible to produce a microfocal spot with an excellent tube rating which lends itself very well for radiography of greater than 2× magnification.

The scanning x-ray system of the present invention can be used to advantage in a wide variety of radiographic systems. For example, increased resolution and elimination of optical density and resolution gradients can be achieved in standard radiographic systems and in radiographic systems having magnification of up to three or four times utilizing the present invention. In addition, the pivoted scanning of tube 10 in the present invention can be used to great advantage in large field angiography, and in linear tomography.

The Radiography Apparatus of FIGS. 5–12B

In FIGS. 5–12B, a preferred embodiment of the present invention used in standard and magnification radiography is shown. The apparatus of FIGS. 5–12B utilizes the pivoted scanning x-ray tube as shown in FIGS. 1 and 2.

In FIG. 5, which is a front elevational view of the apparatus, x-ray tube 10 is pivotally connected to downwardly extending arms 40, which in turn are connected to mounting bracket 42. Tube 10 is pivotally connected to arms 40 so that it may be pivoted about pivot axis 14. As described in conjunction with FIGS. 1 and 2, the pivot axis 14 is perpendicular to the anode-cathode axis, is parallel to the plane of the film, and passes exactly through the center of the focal spot.

In the apparatus of FIG. 5, a table formed by legs 44 and table top 46 provide support for an object (not shown). The x-ray film 18 is located in film tray 48. In the apparatus of FIG. 5, legs 44 of the object table are of a telescoping type, so that table top 46 may be raised and lowered with respect to film 18. The position of table top 46, and therefore the object, with respect to film 18 determines the magnification of the x-ray image recorded on x-ray film 18.

The apparatus of FIG. 5 includes primary slot device 50 and secondary slot device 52. Primary slot device 50 is positioned below collimator 54 and x-ray tube 10 and is positioned above table top 46. Secondary slot device 52 is positioned between table top 46 and film 18.

The purpose of primary and secondary slot devices 50 and 52 is to eliminate secondary radiation which would otherwise fog x-ray film 18. Both primary slot device 50 and secondary slot device 52 include a plurality of slots which are aligned with respect to the primary rays from x-ray tube 10. As tube 10 is pivoted about pivot axis 14, the slots of slot devices 50 and 52 move with respect to the object and x-ray film 18 so that the slots themselves will be blurred and will not appear on the x-ray film 18.

In the apparatus shown in FIG. 5, secondary slot device 52 is supported by legs 56. Film tray 48 is connected to the bottom of secondary slot device 52.

In the embodiment of the present invention shown in FIGS. 5–12B, primary and secondary slot devices 50 and 52 are driven synchronously with the pivoting of x-ray tube 10. Drive means 58 (shown in FIG. 5) includes gear reduction motor 60, clutch/brake 62, and drive chain 64. Pivot arm 66 is linked to drive chain 64 at its lower end and is connected to x-ray tube 10 at its upper end. As drive chain 64 is driven, pivot arm 66 follows drive chain 64 at its lower end, thereby causing x-ray tube 10 to rotate about pivot axis 14. In addition, pivot arm 66 is linked to both primary slot device 50 and secondary slot device 52. For that reason, the pivoting of x-ray tube 10 is synchronized with the movement of primary slot device 50 and secondary slot device 52. As illustrated in FIG. 5 pivot arm 66 preferably moves within a triangular shaped housing 68.

FIGS. 6 and 7 show the connection of pivot arm 66 and x-ray tube 10. Shafts 70 and 72 are connected to tube 10 and extend through arms 40 to permit tube 10 to be rotated about pivot axis 14. Pivot arm 66 is attached to shaft 70 so that as pivot arm 66 moves, tube 10 is rotated about pivot axis 14. This causes scanning of the x-ray beam produced by tube 10.

Primary slot device 50 and secondary slot device 52 are generally similar in construction, and include a plurality of spaced elongated slots through which the primary rays from x-ray tube 10 may pass. Secondary rays such as those produced by scattering of radiation from the object are blocked. Primary slot device 50 is smaller than secondary slot device 52 because it is positioned more closely to x-ray tube 10. In the preferred embodiment shown in FIGS. 5–12B, devices 50 and 52 are of the same general construction, but of different scale.

In order to provide maximum absorption of secondary radition while permitting the primary radiation to pass, the slots of slot devices 50 and 52 have a significant dimension along the direction of travel of the primary rays. In the preferred embodiment of the present invention shown in FIGS. 5–12B, the slot devices 50 and 52 are driven along parallel paths in a linear direction by their linkage to drive chain 64 and pivot arm 66. The slots, however, must remain aligned with the primary rays from tube 10 at all positions along their linear travel. In the preferred embodiments of the present invention, the slots themselves are pivoted about pivot axis 14 so as to maintain the correct angular orientation. In addition, the widths of the slots are maintained constant at all positions along their linear travel.

FIGS. 8–12B show secondary slot device 52 which provides linear movement of an array of slots, while pivoting the slots about pivot axis 14 and maintaining width of the slots constant. Primary slot device 50 is of similar construction, but, as described previously, of a smaller scale. A detailed discussion of secondary slot device 52, therefore, also is applicable to the construction of primary slot device 50.

As shown in FIG. 8, drive chain 64 is driven by motor 60 through chain 74 and clutch/brake 62. The upper and lower runs of chain 64 are oriented parallel to the plane of x-ray film 18 and to the planes of the linear motion of primary and secondary slot devices 50 and 52.

Secondary slot device 52 includes housing 76 containing four parallel guide rods 78a–78d. Guide rods 78a and 78b lie in an upper plane, while guide rods 78c and 78d lie in a lower plane directly below rods 78a and 78b, respectively. All four guide rods 78a–78d have their axial direction parallel to the direction of travel of driven chain 64.

Slidably mounted on guide rods 78a and 78b are upper transverse members 80a and 80b, respectively. Similarly, lower transverse members 80c and 80d are slidably mounted on guide rods 78c and 78d. Transverse members 80a–80d extend in a direction perpendicular and transverse to guide rods 78a–78d.

Upper longitudinal members 82a and 82b extend parallel to guide rods 78a and 78b, and are attached at their one ends to upper transverse member 80a and at their opposite ends to upper transverse member 80b. Similarly, lower longitudinal members 82c and 82d are connected between lower transverse members 80c and 80d.

Pivotally connected between upper longitudinal members 82a and 82b and between lower longitudinal members 82c and 82d are a plurality of metal members 84 and 86 which define slots 88 through which x-ray radiation may pass. As best shown in FIG. 9 and in FIGS. 12A and 12B, each metal member 84 has a generally C-shaped cross-section with a generally vertical portion 84a, a top flange 84b, and a bottom flange 84c. Similarly, each member 86 has a generally C-shaped cross-section which is a mirror image of member 84. Metal member 86 has a generally vertical portion 86a, a top flange 86b, and a bottom flange 86c. In addition, each member 84 has an inverted L-shaped flap 90 attached to vertical portion 84a with the generally horizontal portion of flap 90 extending in the same direction as top and bottom flanges 84b and 84c. Similarly, each member 86 has an L-shaped flap 92 attached to vertical portion 86a with its outward portion extending generally parallel to and extending in the same direction as flanges 86b and 86c.

Top flanges 84b and 86b, bottom flanges 84c and 86c, and flaps 90 and 92 cooperate to block x-ray radiation from passing through secondary slot device 52 except through slots 88. This effectively blocks any secondary radiation from the object, since the slots 88 are oriented to receive only the primary rays.

The width of slots 88 are maintained constant by spacers 94a and 94b, which are located at opposite ends of each slot 88. Spacers 94 maintain the width of slots 88 constant throughout the movement and pivoting of slots 88. Metal members 84 and 86 are attached to and move with spacers 94.

The upper ends of spacers 94a are pivotally connected to upper longitudinal member 82a by pivot pins 96a. Similarly, the upper ends of spacers 94b are pivotally connected to upper longitudinal member 82b by pivot pins 96b. Pivot pins 96a and 96b all lie in a common plane which is parallel to guide rods 78a and 78b. Each pivot pin 96a has a corresponding pivot pin 96b which is connected to longitudinal member 82b, and each pair of pivot pins define a common pivot axis. At the lower ends of spacers 94a and 94b are slots 98a and 98b, respectively. Slots 98a and 98b ride on pins 100a and 100b which are attached to lower longitudinal members 82c and 82d, respectively. Pins 100a and 100b all lie in a common plane which is parallel to guide rod 78c and 78d. Each pin 100a and its corresponding pin 100b defines a common axis.

The secondary slot device 52 illustrated in the Figures is driven from chain 64 so that the slots 88 move linearlly and are pivoted about pivot axis 14 when x-ray tube 10 is rotated about pivot axis 14. In this manner, slots 88 are always oriented to receive primary rays from tube 10. The connection between drive chain 64 and the moving secondary slots 88 is provided through linkage arm 102, which is pivotally connected by pin 104 to chain 64. The upper end of linkage member 102 is connected to upper longitudinal drive member 104a, which extends between the ends of transverse members 80a and 80b. The pivotal connection of linkage member 102 with member 106a is by means of pivot pin 108a. Lower longitudinal drive member 106b extends between the ends of cross members 80c and 80d. Linkage member 102 has a slot 110 which engages pin 108b, which is fixedly connected to member 106b. Pins 104, 108a and 108b are all aligned in a common plane with pivot axis 14.

As chain 64 moves, the lower end of linkage member 102 moves. As a result, members 106a and 106b, and the remainder of the moving slot apparatus moves along guide rails 78a–78d. Because pin 108b is positioned more closely to chain 64 than is pivot pin 108a, the lower members 82c and 82d, and therefore the lower ends of spacers 94a and 94b will experience a larger longitudinal movement than the upper members 82a and 82b and the upper ends of spacers 94a and 94b. The resulting motion transmitted from chain 64 to the moving slot device by linkage arm 102 causes each slot to be translated in a direction parallel to guide rods 78a–78d and also to pivot about pivot axis 14.

The synchronized motion of slots with the pivoting of tube 10 is provided by pivot arm 66 which is fixedly connected near its lower end to linkage member 102 by spacer block 112 and pins 114a and 114b (which ride in slot 110).

The synchronized motion of the slots within primary slot device 50 is provided by linkage arm 116 which is connected by spacer block 118 and pins 120a and 120b to pivot bar 66. The opposite end of linkage member 116 is connected to the moving slot device 50 in a similar manner to the connection of linkage member 102 with secondary slot device 52.

FIGS. 12A and 12B illustrate the operation of the moving slot devices of the present invention in providing a linear translation of the slots 88 while pivoting each slot 88 about pivot axis 14 and maintaining the width of each slot 88 constant. In FIG. 12A, the slots 88 are shown in an essentially vertical orientation, while in FIG. 12B the same slots have been translated to the left and have been pivoted about pivot axis 14.

In order to maintain the width of slots 88 constant, the spacing between adjacent slots is varied. The present invention provides this variable spacing between adjacent slots because members 84 and 86 are not connected to one another. As a result, the spacing between members 84 and 86 can vary except where spacer blocks 94a and 94b positively define their spacing. Flanges 84b and 84c and cooperating flanges 86b and 86c, together with L-shaped members 90 and 92 block all radiation between adjacent slots 88 regardless of the orientation of the slots. The flanges and L-shaped members block radiation without requiring connection of adjacent members 84 and 86.

In operation, pivot arm 66 is originally positioned in its rightmost position as illustrated in FIG. 5. The person of whom the x-ray is to be taken lies horizontally on table top 46 and the operator of the x-ray equipment initiates an x-ray exposure cycle by actuating the switch (not shown).

When the exposure cycle begins, x-rays are emitted from x-ray tube 10 to pass through the object (i.e. the patient's body) and expose x-ray film 18 within film tray 48. The x-rays are in a narrow beam of, for example, 17 inches×2 inches, as has been described previously. Chain 64 begins to be driven so that the lower end of pivot arm 66 moves leftward. The movement of chain 64 causes tube 10 to be rotated about pivot axis 14 and the slots within primary and secondary slot devices 50 and 52 to move synchronously with the rotation of tube 10. When the lower end of pivot arm 66 reaches the opposite (left) end of its travel, the x-ray exposure cycle is terminated.

The apparatus shown in FIGS. 5–12B provides superior radiographs with high resolution, increased contrast, and less patient exposure than has been possible in conventional radiography. Both standard radiographic images and radiography with magnification has been successfully achieved utilzing the apparatus shown in the Figures.

The Large-Scale Angiography Apparatus of FIGS. 13–16.

The present invention, which utilizes the scanning of an x-ray beam by pivoting the x-ray tube about a pivot axis passing through the center of the focal spot, also provides significant advantages when utilized in angiography—the study of blood vessels.

In some cases it is desirable to provide angiographic images of the arteries all the way from the abdomen down to the toes of the patient. In the past, large-scale angiography apparatus has required an extremely high ceiling to mount the x-ray tube a large distance from the patient table in order to provide the necessary field coverage of the x-rays.

Figure 13:
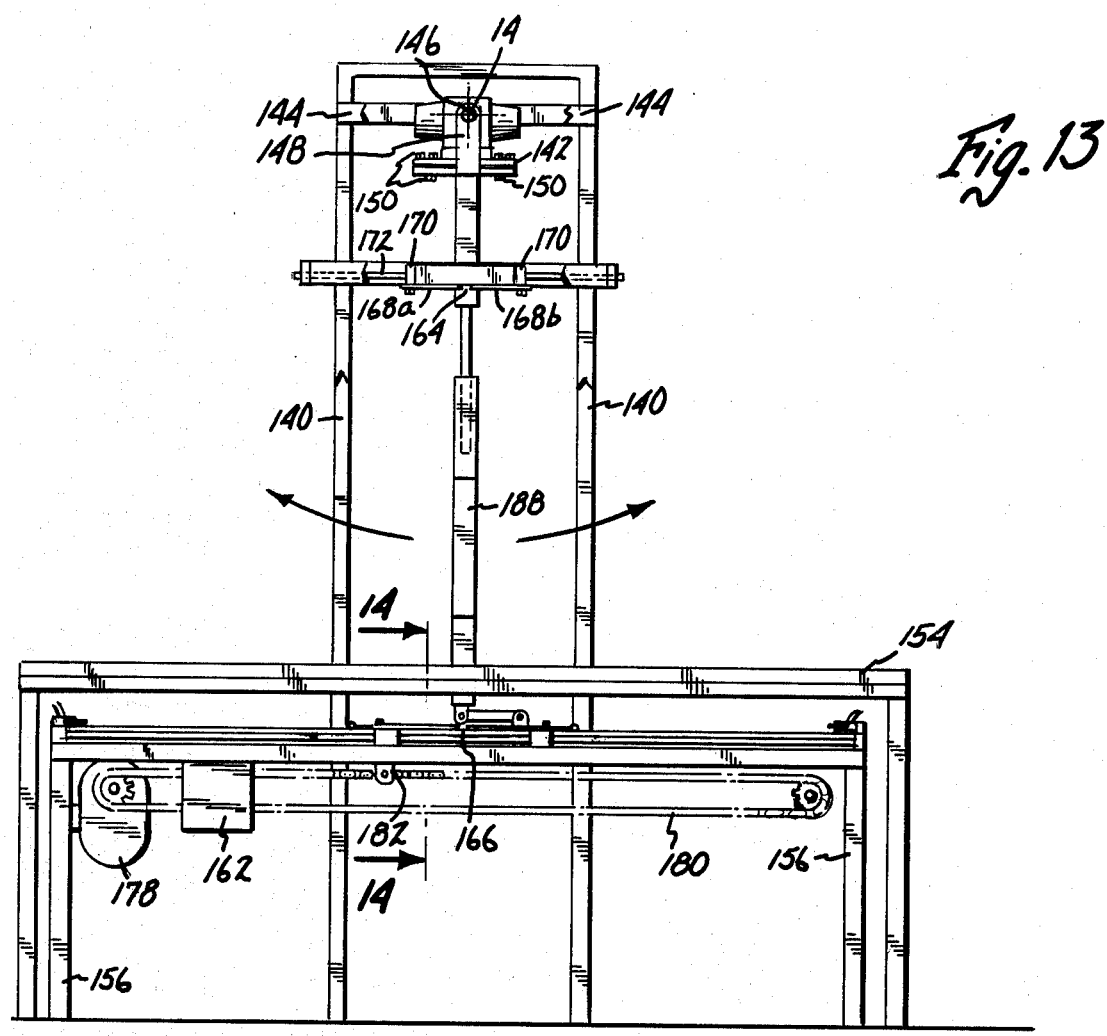
FIG. 13 is a front elevation of a large scale angiography system utilizing the pivotal x-ray scanning of the present invention.
Figure 14:
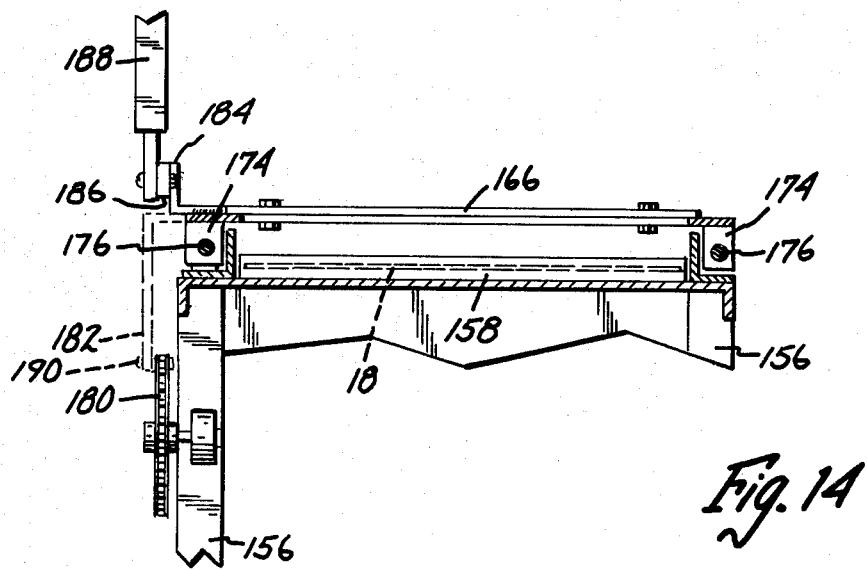
FIG. 14 is a sectional view along line 14—14 of FIG. 13.

The apparatus of the present invention illustrated in FIGS. 13–16 provides large-scale angiography with an apparatus which is smaller and more effective than the prior art devices. FIGS. 13 and 14 illustrate the structure of the apparatus of the preferred embodiments, while FIGS. 15 and 16 schematically illustrate the system of FIGS. 13 and 14.

As shown in the Figures, x-ray tube 10 is again mounted to rotate about pivot axis 14. Tube 10 is supported near the top of frame 140 by mounting bracket 142. Tube 10 is fixedly connected to bracket 142. Frame 140 has a pair of cross members 144 (one of which is partially broken away in FIG. 13) having holes which rotatably receive a pair of shafts 146. Mounting bracket 142 has a pair of upstanding arms 148 to which shafts 146 are connected. As bracket 142 is rotated about the pivot axis 14 defined by shafts 146, tube 10 is also rotated. Adjustment screws 150 permit adjustment of the position of tube 10 with respect to bracket 142 so that the pivot axis 14 is precisely positioned to pass through the center of the focal spot of tube 10. Adjustment screws 150 permit adjustment both in a horizontal and a vertical direction.

The patient is supported on object table 154. A second table 156 is located below object table 154 and supports a film pack 158 containing the x-ray film 18. As shown in FIG. 13, the length of the film pack may be essentially the entire length of the patient lying on the object table. As a result, an extremely long angiographic image may be produced with the apparatus. Film vacuum hold 162 applies a vacuum between film pack 158 and table 156 to hold film pack 158 and film 18 securely in position during an exposure cycle.

As in the standard radiography apparatus shown in FIGS. 5–12B, the large-scale angiography apparatus utilizes moving primary and secondary slots. The apparatus of FIGS. 13–16, however, utilizes only a single primary slot 164 and a single secondary slot 166.

Primary slot 164 is defined by a pair of metal plates 168a and 168b. Plates 168a and 168b are attached to guide blocks 170, which ride on a pair of guide rods 172.

Similarly, secondary slot 166 is defined by a pair of plates 174a and 174b, which are connected to guide blocks 174, which in turn ride on a pair of guide rods 176.

Primary slot 164, secondary slot 166, and x-ray tube 10 are driven synchronously by motor 178 through chain drive 180, linkage arm 182, bracket 184, linkage 186, and pivot arm 188. Linkage arm 182 is connected to drive chain 180 by pivot pin 190, and is attached at its upper end to the secondary slot device. Bracket 184 and linkage 186 connect guide blocks 174 of the secondary slot device with pivot arm 188. The primary slot device is similarly connected to pivot bar 188, and bracket 142 is connected to pivot arm 188 so that movement of pivot arm 188 causes tube 10 to rotate about pivot axis 14.

As chain drive 180 moves, secondary slot 166 is driven from right to left in FIGS. 13 and 15 and pivot arm 188 pivots from right to left about pivot axis 14. This causes primary slot 164 to move from left to right in a linear motion, and causes x-ray tube 10 to rotate about pivot axis 14.

In operation, x-ray beam 12 is scanned in a narrow beam defined by slots 164 and 166 from one end of x-ray film 160 to its opposite end. Because the movement of x-ray tube 10 is a rotational movement about pivot axis 14 rather than a lateral translation, problems of vibration are eliminated. An extremely wide field coverage is provided by scanning the narrow x-ray beam 12 rather than requiring the beam to cover the entire field of interest simultaneously.

In some applications, the rate of scanning of the x-ray beam can be coordinated with the rate of travel of dye through the patient's body. In this manner, the x-ray beam can effectively be scanned so as to follow the travel of the dye down the person's body.

As in the case of the standard radiography apparatus described previously, the large-scale angiography apparatus of FIGS. 13–16 provides improved resolution, increased contrast, and less patient exposure than the prior art apparatus. In addition, the apparatus of the present invention is significantly smaller than the prior art apparatus providing the same field coverage. In particular, the present apparatus can fit in a conventional size room, and does not require an abnormally high ceiling. As a result, it can find application in areas where a special room with a high ceiling is not feasible or desirable.

Figure 17:
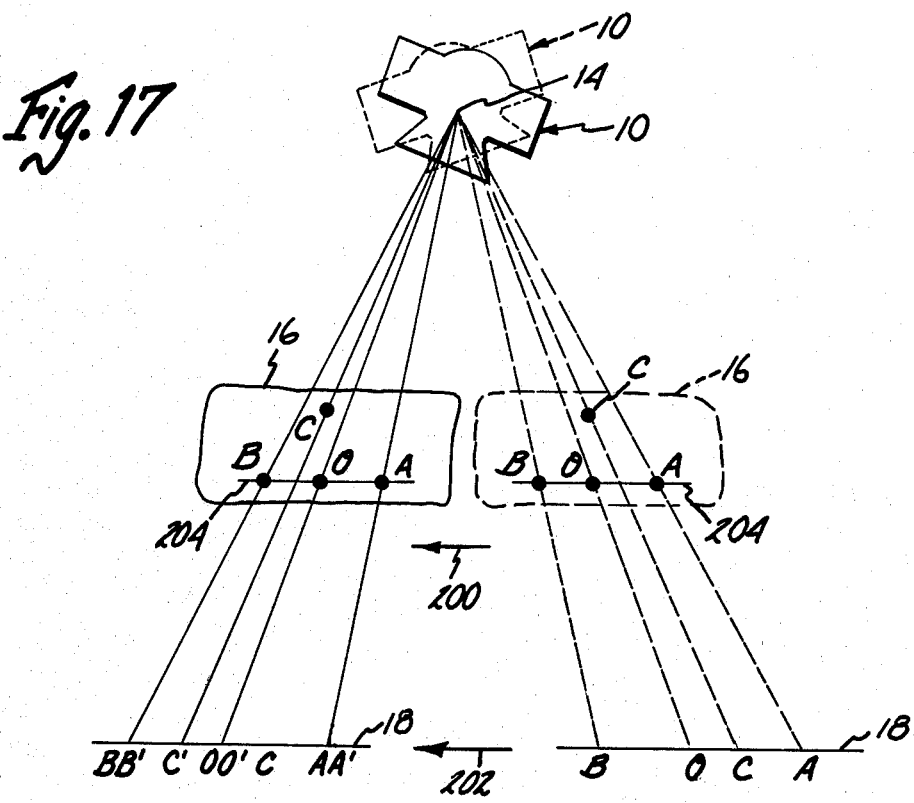
FIGS. 17 and 18 are diagrammatic views illustrating the operation of the present invention to produce linear tomographs.
Figure 18:
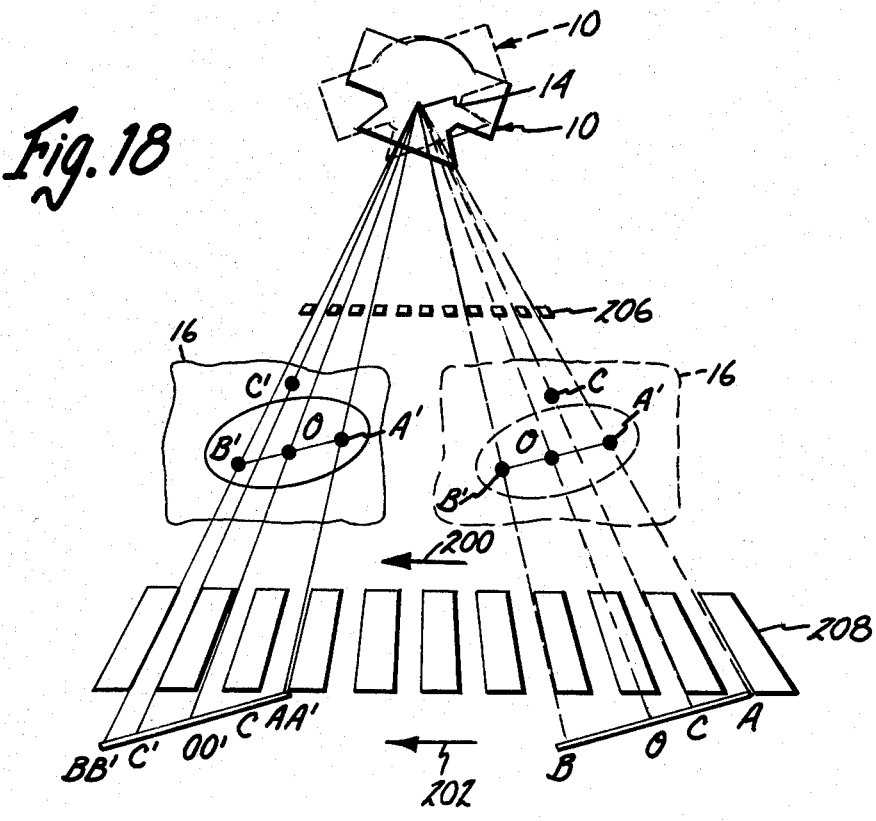

The Linear Tomography Apparatus of FIGS. 17 and 18

As described in the previous embodiments, the scanning of an x-ray beam by pivoting the x-ray tube about a pivot axis passing through the center of the focal spot provides significant improvement in standard radiography and in large-scale angiography. FIGS. 17 and 18 show another embodiment of the present invention, and illustrate the advantageous use of the pivoted scanning x-ray tube of the present invention in linear tomography.

In the embodiment illustrated schematically in FIG. 17, x-ray tube 10 is again pivoted about pivot axis 14, which passes through the center of the focal spot and is parallel to the plane of the x-ray film 18. As x-ray tube 10 is rotated about pivot axis 14, object 16 and x-ray film 18 are moved linearlly parallel to one another in synchronous fashion.

In FIG. 17, x-ray tube 10 is shown in two positions. In the first position, tube 10, x-ray beam 12, object 16 and film 18 are all shown in phantom. In the second position, tube 10 has been rotated about axis 14 and is shown in solid lines, as are beam 12, object 16 and film 18.

At the same time that tube 10 is being rotated about axis 14 to the second positon, object 16 and film 18 are being translated to the left as shown in FIG. 17. The translation of object 16 and film 18 is designated by arrows 200 and 202, respectively.

In the present invention, as shown in FIG. 17, points lying within focal plane 204 (which is within object 16) are projected at the same location on film 18 throughout the scan of x-ray beam 12 and the movement of object 16 and film 18. Points lying outside focal plane 204 will be blurred, so that true tomograms are produced.

This is illustrated in FIG. 17 by points A, O and B which lie in plane 204 and by point C which lies above plane 204. At the beginning of the scan, when object 16 and film 18 are at their first (right) position in FIG. 17, the projection of point C on film 18 is located between the projections of points O and A.

As tube 10 is rotated about pivot axis 14, object 16 and film 18 are translated to the left as illustrated by arrows 200 and 202 until they reach the second position illustrated in FIG. 15. Throughout the movement of object 16 and film 18, points B, O and A of plane 204 continue to be projected on the same positions on film 18. This is illustrated by the second position in which the projection of points B, O and A on film 18 are designated as B', O', and A'. As shown, projections B and B', projections O and O', and projections A and A' correspond.

In the case of point C, however, which falls outside of plane 204, its projection changes as tube 10 is rotated and object 16 and film 18 are translated. In the second position, the projection (C') of point C on film 18 is now to the left of the projection of point O–O'. The changing positions of the projection of point C (and all other points lying out of the plane 204), causes these points to be blurred, while the projections of points lying in plane 204 reinforce one another to produce a linear tomogram of superior diagnostic quality.

The movement of object 16 and film 18 in synchronism with the rotation of tube 10 is preferably provided by a pivot arm which is driven by an appropriate drive such as a drive chain in a manner generally similar to the embodiments which have been previously discussed. The pivot arm (not shown in FIG. 15) is linked to tube 10, to the table on which object 16 rests, and to the tray containing film 18.

FIG. 18 illustrates another preferred embodiment of the linear tomography apparatus of the present invention. The apparatus schematically illustrated in FIG. 18 is generally similar to the apparatus of FIG. 17 with two important modifications. First, a set of primary slots 206 is positioned between tube 10 and object 16, and a second set of secondary slots 208 is positioned between object 16 and film 18. Primary and secondary slots 206 and 208 provide efficient absorption of secondary radiation without increasing the radiation dose to the patient. Since object 16 and film 18 both move as tube 10 is rotated, primary slots 206 and secondary slots 208 may remain stationary and will be efficiently blurred.

Second, film 18 may be tilted at an angle with respect to horizontal as shown in FIG. 18. As a result, it is possible for the apparatus of FIG. 18 to obtain tomographic cuts parallel to the organ of interest even if that organ does not lie parallel to the table top. In standard laminography only cuts parallel to the table top are possible. The present invention, therefore, allows greater interpretation and reduction of the number of cuts in order to study an organ which is difficult to image using classical methods, such as the kidney or common duct. These organs are not parallel to the table top and consequently, in the prior art techniques the upper and lower poles of the kidney cannot be seen simultaneously on the same tomogram. The additional cuts required in the prior art to study an organ increases the exposure to the patient, which is clearly undesirable. Using the present invention, the organ may be visualized tomographically along its long axis by tilting the plane of film 18 and therefore the number of tomographic cuts and the amount of exposure of x-rays to the patient can be significantly decreased.

The use of slots 206 and 208 in the system of FIG. 18 reduces scattered radiation much more effectively than the prior art radiographic grids. Residual radiographic fog is decreased from about 35 percent (with a grid) to approximately 8 percent. The dose to the patient, therefore, is much lower as compared with standard radiographic grids.

The scanning beam linear tomography illustrated in FIGS. 17 and 18 has many important advantages over the prior art linear tomography. First, true linear tomograms can be performed along the long axis of the body, as in standard tomography. Second, vibration of x-ray tube 10 is eliminated since it is merely rotated about pivot axis 14, rather than being translated in position. Third, a 100 micron focal spot x-ray tube may be used, as described in conjunction with the other embodiments of the present invention, thereby resulting in improved resolution and definition. Fourth, a stationary primary and secondary slot system as shown in FIG. 18 markedly reduces scatter, thereby resulting in better image contrast. Fifth, radiographic cuts parallel to the long axis of organs are feasible by tilting film 18, thereby reducing the number of necessary tomographic layers. Sixth, the patient's exposure dose is reduced since no Bucky is used. Seventh, a book film cassette no longer degrades diagnostic information and further reduces radiation to the patient.

Conclusion

The x-ray apparatus of the present invention provides significant advantages for a wide range of radiographic applications. The scanning pivoted x-ray tube utilized in the present invention has been successfully used in standard radiography, magnification radiography, linear tomography, and large-scale angiography. The significant advantages of the present invention can also be applied to a wide range of other radiographic applications.

Although the present invention has been described with reference to preferred embodiments, persons skilled in the art will recognize that changes may be made in form and detail without departing from the spirit and scope of the invention.

What is claimed is:

1. An x-ray apparatus for producing x-ray images of an object, the x-ray apparatus comprising:

x-ray sensitive means positioned on one side of the object for receiving x-rays which have passed through the object, the x-ray sensitive means defining a field over which x-rays are received, the field having a first dimension in a first direction and a second dimension in a second direction;

x-ray source means positioned on an opposite side of the object from the x-ray sensitive means for providing a narrow x-ray beam having a first dimension at the field defined by the x-ray sensitive means which is at least equal to the first dimension of the field having a second dimension at the field defined by the x-ray sensitive means which is less than the second dimension of the field and less than the first dimension of the narrow beam, the x-ray source means including an x-ray tube in which an electron stream from a cathode is directed along an anode-cathode axis to strike a focal spot on a target surface of an anode to produce x-rays, the target surface being inclined with respect to a first plane which (1) is perpendicular to the anode-cathode axis and (2) passes through the center of the focal spot; and pivoting means for pivoting the x-ray source means about a pivot axis to cause the narrow x-ray beam to be scanned in the second direction across the field defined by the x-ray sensitive means to cover the second dimension of the field, wherein the pivot axis (1) passes exactly through the center of the focal spot, (2) is perpendicular to the anode-cathode axis, (3) lies in the first plane, (4) is parallel to the field defined by the x-ray sensitive means, and (5) is parallel to the first direction so that as the x-ray source means is pivoted by the pivoting means, the center of the focal spot remains stationary.

2. The x-ray apparatus of claim 1 wherein the x-ray source means further comprises:

means mounted to and movable with the x-ray tube as the x-ray tube is pivoted for limiting the x-rays emitted from the x-ray tube to the narrow beam which is located, with respect to the first plane, on a side of the first plane which is furthest from the cathode.

3. The x-ray apparatus of claim 1 and further comprising:

primary slot means positioned between the tube and the object;

secondary slot means positioned between the object and the x-ray sensitive means;

means for causing relative motion, synchronized with pivoting of the x-ray tube, of the primary and secondary slot means with respect to the object and the x-ray sensitive means.

4. The invention of claim 3 wherein the means for causing relative motion comprises:
   first drive means for driving the primary slot means in synchronism with the pivoting of the x-ray tube; and
   second drive means for driving the secondary slot means in synchronism with the pivoting of the x-ray tube.

5. The invention of claim 1 wherein the pivoting means comprises:
   pivot arm means having an upper end connected to the x-ray tube; and
   drive means connected to a lower end of the pivot arm means for driving the lower end to pivot the pivot arms means and the x-ray tube about the pivot axis.

6. The invention of claim 5 and further comprising:
   primary slot means positioned between the tube and the object;
   means connecting the primary slot means and the pivot arm means to drive the primary slot means in synchronism with pivoting of the x-ray tube;
   secondary slot means positioned between the object and the x-ray sensitive means; and
   means connecting the pivot arm means and the secondary slot means to drive the secondary means in synchronism with pivoting of the x-ray tube.

7. The apparatus of claim 6 wherein the drive means comprises a chain drive.

8. The invention of claim 7 wherein the means connecting the pivot arm means and the secondary slot means comprises:
   linkage means linking the chain drive and the secondary slot means; and
   connecting means connecting the secondary slot means and the pivot arm.

9. An x-ray apparatus for producing x-ray images of an object, the apparatus comprising:
   a source of x-rays which includes an x-ray tube in which an electron stream from a cathode is directed along an anode-cathode axis to strike a focal spot on a target surface of an anode to produce x-rays, the target surface being inclined with respect to a plane which is perpendicular to the anode-cathode axis and which passes through the focal point;
   x-ray sensitive means positioned so that the object is interposed between the source of x-rays and the x-ray sensitive means;
   pivoting means for pivoting the x-ray tube about a pivot axis which passes exactly through the center of the focal spot, is essentially perpendicular to the anode-cathode axis, and is essentially parallel to a plane defined by the x-ray sensitive means;
   primary slot means positioned between the tube and the object;
   secondary slot means positioned between the object and the x-ray sensitive means;
   first drive means for driving the primary slot means in synchronism with the pivoting of the x-ray tube; and
   second drive means for driving the secondary slot means in synchronism with the pivoting of the x-ray tube;
   wherein the primary slot means comprises:
      movable primary slot support means driven by the first drive means;
      a plurality of primary slots supported by the primary slot support means to pivot about pivot axis while the primary slot support means is driven by the first drive means;
      means for maintaining widths of the primary slots substantially constant while the primary support means is driven by the first drive means; and
      means for varying spacing between adjacent primary slots while the primary slot support means is driven by the first drive means.

10. The invention of claim 9 wherein the primary slot support means is moved by the first drive means essentially parallel to the plane defined by the x-ray sensitive means.

11. An x-ray apparatus for producing x-ray images of an object, the apparatus comprising:
   a source of x-rays which includes an x-ray tube in which an electron stream from a cathode is directed along an anode-cathode axis to strike a focal spot on a target surface of an anode to produce x-rays, the target surface being inclined with respect to a plane which is perpendicular to the anode-cathode axis and which passes through the focal point;
   x-ray sensitive means positioned so that the object is interposed between the source of x-ray means and the x-ray sensitive means;
   pivoting means for pivoting the x-ray tube about a pivot axis which passes exactly through the center of the focal spot, is essentially perpendicular to the anode-cathode axis, and is essentially parallel to a plane defined by the x-ray sensitive means;
   primary slot means positioned between the tube and the object;
   secondary slot means positioned between the object and the x-ray sensitive means;
   first drive means for driving the primary slot means in synchronism with the pivoting of the x-ray tube; and
   second drive means for driving the secondary slot means in synchronism with the pivoting of the x-ray tube;
   wherein the secondary slot means comprises:
      movable secondary slot support means driven by the second drive means;
      a plurality of secondary slots supported by the secondary slot support means to pivot about the pivot axis while the secondary slot support means is driven by the second drive means;
      means for maintaining widths of the secondary slots substantially constant while the secondary support means is driven by the second drive means; and
      means for varying spacing between adjacent secondary slots while the secondary slot support means is driven by the second drive means.

12. The invention of claim 11 wherein the secondary slot support means is moved by the second drive means essentially parallel to the plane defined by the x-ray sensitive means.

13. An x-ray apparatus for producing x-ray images of an object, the apparatus comprising:
   a source of x-rays which includes an x-ray tube in which an electron stream from a cathode is directed along an anode-cathode axis to strike a focal spot on a target surface of an anode to produce x-rays, the target surface being inclined with respect to a plane which is perpendicular to the anode-cathode axis and which passes through the focal point;

x-ray sensitive means positioned so that the object is interposed between the source of x-rays and the x-ray sensitive means;

pivoting means for pivoting the x-ray tube about a pivot axis which passes exactly through the center of the focal spot, and is essentially perpendicular to the anode-cathode axis, and is essentially parallel to a plane defined by the x-ray sensitive means, wherein the pivoting means comprises:

pivot arm means having an upper end fixedly connected to an x-ray tube; and drive means connected to a lower end of the pivot arm means for driving the lower end to pivot simultaneously the pivot arm means and the x-ray tube about the pivot axis;

primary slot means positioned between the tube and the object;

means connecting the primary slot means and the pivot arm means to drive the primary slot means in synchronism with pivoting of the x-ray tube;

secondary slot means positioned between the object and the x-ray sensitive means;

means connecting the pivot arm means and the secondary slot means for driving the secondary slot means in synchronism with pivoting of the x-ray tube; and wherein the primary and secondary slot means each comprise:

a pair of generally parallel upper guide rods and a pair of generally parallel lower guide rods;

an upper slot support means movable on the upper guide rods and a lower slot support means movable on the lower guide rods;

slot defining members spaced from one another to define a plurality of generally parallel slots through which primary radiation from the x-ray tube may pass, wherein the slot defining members comprise a plurality of members oriented essentially parallel to a path of primary radiation from the x-ray tube;

a plurality of spacers which are pivotally connected to the upper slot support means proximate their upper ends and are slidably connected to the lower slot support means proximate their lower ends, the spacers defining a width of the slot.

14. The invention of claim 13 wherein each spacer has a longitudinal slot at its lower end which engages a pin connected to the lower slot support means for slidably connecting the spacer to the lower slot support means.

15. The invention of claim 14 wherein the upper and lower slot support means are connected to the pivot arm means.

16. The invention of claim 13 and further comprising:
radiation blocking means connected to the slot defining members for blocking radiation from passing between adjacent slots defined by the slot defining members.

17. The invention of claim 16 wherein the radiation blocking means comprise flanges at upper and lower ends of the slot defining members.

18. The invention of claim 17 wherein the radiation blocking means further comprise metal flap means attached to the slot defining members to block radiation passing between adjacent slots.

* * * * *